(12) United States Patent
Gruner et al.

(10) Patent No.: US 7,737,812 B2
(45) Date of Patent: Jun. 15, 2010

(54) METHOD FOR OPENING HOLLOW STRUCTURES MADE FROM MAGNETIC NANOPARTICLES

(75) Inventors: Markus Gruner, Duisburg (DE); Alfred Hucht, Duisburg (DE); Peter Entel, Köln (DE); Michael Farle, Mülheim/Ruhr (DE)

(73) Assignee: Universität Duisburg-Essen, Essen (DE)

( * ) Notice: Subject to any disclaimer, the term of this patent is extended or adjusted under 35 U.S.C. 154(b) by 70 days.

(21) Appl. No.: 11/913,961

(22) PCT Filed: May 9, 2006

(86) PCT No.: PCT/EP2006/004305

§ 371 (c)(1),
(2), (4) Date: Nov. 9, 2007

(87) PCT Pub. No.: WO2006/119957

PCT Pub. Date: Nov. 16, 2006

(65) Prior Publication Data

US 2008/0191828 A1   Aug. 14, 2008

(30) Foreign Application Priority Data

May 10, 2005 (DE) .............. 10 2005 022 274
Aug. 11, 2005 (DE) .............. 10 2005 038 304

(51) Int. Cl.
*H01F 1/00* (2006.01)
(52) U.S. Cl. ............... 335/296; 977/906; 977/907
(58) Field of Classification Search ......... 977/906–907; 335/296
See application file for complete search history.

(56) References Cited

U.S. PATENT DOCUMENTS

2007/0196281 A1* 8/2007 Jin et al. .............. 424/9.34

FOREIGN PATENT DOCUMENTS

| DE | 4309333 | 9/1994 |
| DE | 19606804 | 8/1997 |
| DE | 19745890 | 3/1999 |
| DE | 10141674 | 3/2002 |

OTHER PUBLICATIONS

Tartaj et al., "From Hollow to Dense Spheres: Control of Dipolar Interactions by Tailoring the Ar-chitecture in Colloidal Aggregates of Superparamagnetic Iron Oxide Nanocrystals", Advanced Material, Mar. 18, 2004, vol. 16, No. 6, pp. 529-533.
Ullakko et al. "Large Magnetic-Field-Induced Strains in Ni2MnGa single crystals", Appl.-Phys. Lett. 69 (13), 23. Sep. 1996, pp. 1966-1968.
Caruso et al. "Magnetic Nanocomposite Particles and Hollow Spheres Constructed by a Sequential Layering Approach", Chem. Mater. 2001, 13, 109-116.

(Continued)

*Primary Examiner*—Ramon M Barrera
(74) *Attorney, Agent, or Firm*—Jason H. Vick; Sheridan Ross, P.C.

(57) ABSTRACT

A method is proposed for opening of hollow structures made of magnetic nanoparticles. To avoid an unwanted heating, the hollow structures are opened by a strong, preferably rotating magnetic field. The method can be used, in particular, for the releasing of a diagnostic and/or therapeutic agent in a human or animal body.

16 Claims, 1 Drawing Sheet

OTHER PUBLICATIONS

Caruso "Hollow Capsule Processing through Colloidal Templating and Self-Assembly", Chem. Eur. J. 2000, 6, No. 3.

Alexiou et al. "Locoregional Cancer Treatment with Magnetic Drug Targeting", Cancer Research 60, 6641-6648, Dec. 1, 2000.

Goodwin et al., "Targeting and Retention of Magnetic Targeted Carriers (MTCs) Enhancing Intra-Arterial Chemotherapy", Journal of Magnetism and Magnetic Materials 194 (1999) 132-166.

Babincová et al., "Laser Triggered Drug Release from Magnetoliposomes", Journal of Magnetism and Magnetic Materials 194 (1999) 163-166.

Kuznetsow et al., "New Ferro-Carbon Adsorbents for Magnetically Guided Transport of Anti-Cancer Drugs", Journal of Magnetism and Magnetic Materials 194 (1999) 22-30.

Kuznetsow et al., "Application of Magnetic Liposomes for Magnetically Guided Transport of Muscle Re-laxants and Anti-Cancer Photodynamic Drugs", Journal of Magnetism and Magnetic Materials 225 (2001) 95-100.

Voigt et al., "Novel Polyelectrolyte Multilayer Micro- and Nanocapsules as Magnetic Carriers", Journal of Magnetism and Magnetic Materials 225 (2001) 59-66.

Pankhurst et al., "Applications of Magnetic Nanoparticles in Biomedicine", J. Phys. D: Appl. Phys. 36 (2003) R167-R181.

Tartaj et al., "The Preparation of Magnetic Nanoparticles for Applications in Biomedicine", J. Phys. D: Appl. Phys. 36 (2003) R182-R197.

Safarik et al., "Magnetic Nanoparticles and Biosciences", Monatshefte für Chemie 133, 737-759 (2002).

Knipping et al., "Synthesis and Characterization of Nanowires formed by Self-Assembled Iron Parti-cles", Nanotechnology 15 (2004) 1665-1670.

Mehlig et al., "Hybrid Monte Carlo Method for Condensed-Matter Systems", Physical Review B, vol. 45, No. 2, Jan. 1, 1992-II.

International Search Report for International (PCT) Patent Application No. PCT/EP2006/004305, mailed Jan. 25, 2007.

Written Opinion for International (PCT) Patent Application No. PCT/EP2006/004305, mailed Jan. 25, 2007.

International Preliminary Report on Patentability for International (PCT) Patent Application No. PCT/EP2006/004305, mailed Jan. 25, 2007.

\* cited by examiner

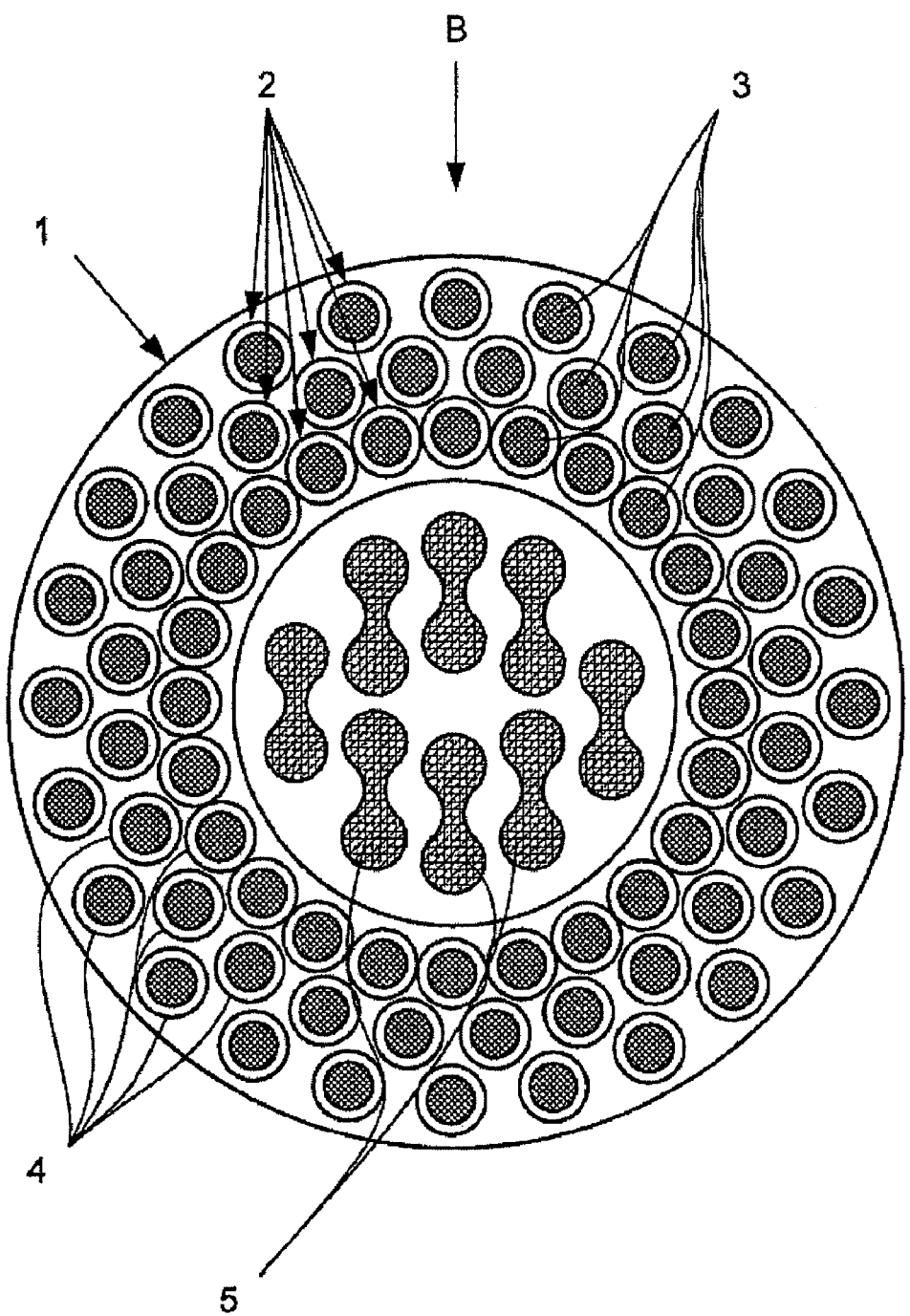

METHOD FOR OPENING HOLLOW STRUCTURES MADE FROM MAGNETIC NANOPARTICLES

CROSS REFERENCE TO RELATED APPLICATION

This application is a national stage application under 35 U.S.C. 371 of PCT Application No. PCT/EP2006/004305 having an international filing date of May 9, 2006, which designated the United States, which PCT application claimed the benefit of German Application No. 10 2005 022 274.9 filed May 10, 2005 and German Application No. 10 2005 038 304.1 filed Aug. 11, 2005, the entire disclosure of each being incorporated herein in their entirety.

The present invention concerns a method for opening of hollow structures made of magnetic nanoparticles, and uses of this method.

So-called "Drug Targeting" is familiar. Using a magnetic field applied from the outside, a magnetically interacting drug is held or concentrated in the blood in a desired region of the human or animal body. The drug is magnetically configured for this, or it is connected to a magnetic particle, molecule, or the like.

Recently, hollow structures of magnetic nanoparticles, especially hollow spheres, tubes, or the like, have become known. These hollow structures can likewise be employed for the mentioned "Drug Targeting" or other tasks. In the case of "Drug Targeting," a drug present in the hollow structures is liberated by irradiation with laser light or high-frequency electromagnetic fields. This produces an unwanted or even problematic heating, particularly of the drug and the surrounding tissue. Other methods are based on chemical or mechanical destruction and thus do not have local action.

The basic problem of the present invention is to indicate a method for the opening of hollow structures made of magnetic nanoparticles, as well as uses for the method, wherein the opening can occur in a desired local region without (substantial) heating.

The above problem is solved by a method per claim 1 or a usage according to one of the dependent claims. Advantageous embodiments are the subject of the subclaims. A basic notion of the present invention is to expose the hollow structures to a strong magnetic field, at least one not producing any significant heating of the hollow structures or the surroundings, so that the interaction of magnetic dipoles of neighboring nanoparticles exceeds the binding energy of these nanoparticles or comes at least so close to this binding energy that the nanoparticles become separated, thus opening the hollow structures or, in particular, even cutting them open. This makes possible a nonthermal opening of the hollow structures.

The proposed method can be used, in particular, to release substances present in the hollow structures in a fluid flow in a desired region, possibly one which is not accessible, by opening of the hollow structures. In particular, this enables a liberation of a diagnostic and/or therapeutic substance or drugs in the human or animal body, without producing an unwanted heating.

The proposed opening of the hollow structures, however, can also be used as a onetime actuator activation. The hollow structures then constitute actuators in the nanometer range.

Moreover, the proposed opening of the hollow structures can also be used for composites or other materials which contain the hollow structures, in order to modify the material properties.

Other benefits, features, characteristics and aspects of the present invention will emerge from the claims and the following specification of a preferred embodiment by means of the drawing. The single FIGURE shows:

a schematic representation of a hollow structure made of magnetic nanoparticles in the closed state, with a substance taken up inside it.

The representation is not true to scale and serves merely for purposes of illustration.

The represented hollow structure 1 is made up of a plurality of magnetic nanoparticles 2. It is preferably in the shape of a hollow sphere. Alternatively, however, the hollow structure 1 can also be tubular or have any other shape.

The nanoparticles 2 preferably have a magnetic core 3 and, if need be, a preferably nonmagnetic envelope 4.

The mean diameter of the nanoparticles 2 is preferably between 1 nm and 1000 nm, especially basically 5 to 100 nm. This accounts for the term "nanoparticle."

The nanoparticles 2 and their cores 3 are preferably ferromagnetic or superparamagnetic. In particular, the cores 3 consist of ferritic material or the like. The envelopes 4 serve, in particular, to protect the magnetic cores 3, especially against oxidation etc., and/or provide a possibility of manipulating the bond between the nanoparticles 2—for example, by appropriate choice of their thickness or magnetic properties. The nanoparticles 2 can be combined into the represented hollow structure 1 or other hollow structures.

Preferably, the thickness of the envelopes 4 is 0.5 to 2 nm, in particular around 1 nm. Based on a mean core diameter of 12 nm, one then gets a diameter of around 14 nm on average for the nanoparticle 2.

Preferably, the diameter of the hollow structures 1 is between 0.1 μm and 10 μm, especially 0.2 μm to 1 μm. The shell of the hollow structures 1 can contain several radial layers of nanoparticles 2. For three monolayers or a thickness of around 40 nm of the shell, one gets an overall diameter of the hollow structure 1 of around 200 to 300 nm, for example, for nanoparticles 2 with a mean diameter of around 14 nm.

The nanoparticles 2 each have magnetic moments (dipoles). The magnetic moments preferably amount to around $2 \cdot 10^{-19}$ $Am^2$ to $5 \cdot 10^{-18}$ $Am^2$, especially around $3 \cdot 10^{-19}$ $Am^2$ to $5 \cdot 10^{-19}$ $Am^2$. For a core diameter of around 12 nm and iron as the core material, the magnetic moment amounts to around $3.7 \cdot 10^{-19}$ $Am^2$.

The mentioned hollow structures 1 or comparable hollow structures are stable at room temperature or the temperature of the human or animal body. In particular, at such temperatures the thermal energy $E_{Therm}$ is around 0.078 eV. The binding energy $E_{Bind}$ of the hollow structure 1 is estimated to be preferably 0.1 to 0.3 eV, especially around 0.15 to 0.25 eV. The binding energy $E_{Bind}$ of the hollow structures 1 is thus larger than the thermal energy $E_{Therm}$.

It is proposed to achieve an opening, especially an undoing or a cutting open of the hollow structures 1, by applying a strong external magnetic field B. The magnetic field B, in particular, is created by a permanent magnetic (not shown) or by an electromagnetic (not shown).

Preferably, the magnetic field B is at least essentially static and/or homogeneous. However, it can also be inhomogeneous if need be, especially for the concentrating of hollow structures 1 in a desired region of space.

It has been determined that the magnetic field B, when sufficiently strong, results in a migration or even a separation of nanoparticles 2. Accordingly, the hollow structure 1 is opened or destroyed.

Especially preferably, the magnetic field B is rotated or turned. The frequency of rotation is preferably high enough that the hollow structure 1 cannot follow the rotation. Moreover, the rotation frequency is proposed to be low enough to avoid an unwanted warming or heating of the hollow structures 1 and/or the surroundings, especially surrounding bodily tissue, blood, or the like.

Especially preferably, the rotation frequency is greater than 100 Hz, especially greater than 1 kHz. Especially preferably, the rotation frequency is less than 100 kHz, especially less than 10 kHz.

The rotating or turning of the magnetic field B produces a kind of cutting open of the hollow structures 1 along an equatorial plane, preferably running at least basically perpendicular to the direction of turning of the magnetic field B.

The proposed opening of the hollow structures 1 by the sufficiently strong magnetic field B thus produces no significant or relevant heating, even for a rotating magnetic field B. Thus, a nonthermal opening or destruction of the hollow structures 1 is made possible by the proposal.

The opening of the hollow structures 1 by the magnetic field B can be accounted for in that the magnetic moments or dipoles of neighboring nanoparticles 2 are oriented by the external magnetic field B at least essentially parallel to each other in the region of the poles of the hollow structures 1. The parallel orientation results in a repulsion of neighboring nanoparticles 2 in the plane perpendicular to the magnetic field. Furthermore, there is an attraction between neighboring nanoparticles 2 arranged one behind the other in the direction of the magnetic field. Therefore, a shifting or even a separation occurs for neighboring nanoparticles 2 when the dipole energies or forces are large enough. This explains how an opening or destruction of the hollow structures 1 is possible by means of the strong magnetic field B.

The strength of the magnetic field B is preferably such that a repulsion energy or dipole energy $E_{Dipol}$ of at least 0.01 eV, especially at least 0.05 eV or more, is preferably achieved between neighboring nanoparticles 2—with respect to the magnetic field B at least in the polar regions of the hollow structures 1. The repulsion energy or dipole energy $E_{Dipol}$ can then, together with the thermal energy $E_{Therm}$, reach or surpass the binding energy $E_{Bind}$. An opening or destruction of the hollow structures 1 will then occur at once.

However, by theoretical estimates and extensive simulations it has also been established that even if the sum of the dipole energy $E_{Dipol}$ and thermal energy $E_{Therm}$ does not exceed the binding energy $E_{Bind}$, an opening of the hollow structures 1 can occur. This suggests that a migration of nanoparticles 2 brought about here in particular by the rotation or turning of the magnetic field B is responsible for a damaging of the hollow structures 1. This dynamic effect is analytically hard to describe. The rotating magnetic field B is responsible for the migration. The binding energy $E_{Bind}$ in this case represents an energy barrier, which can evidently be overcome by thermal fluctuations. Preferably, the sum of thermal energy $E_{Therm}$ and dipole energy $E_{Dipol}$ is at least 10%, especially at least 30%, very preferably 50% or more of the binding energy $E_{Bind}$, in order to make possible an opening of the hollow structures 1 in relatively short time.

The strength of the magnetic field B is preferably at least 0.1 T, especially around 0.2 T to 1 T.

Most especially preferably, the magnetic field B is at least essentially $(3\mu_0\mu)/(2\pi a^3)$ or more. Here, $\mu_0$ is the magnetic induction constant $4\pi \cdot 10^{-7}$ VsA$^{-1}$ m$^{-1}$, $\mu$ is the magnetic moment of the interacting nanoparticles 2, and a is the mean diameter of the nanoparticle 2 or the center-to-center distance between neighboring nanoparticles 2. From this estimate, using the parameters already mentioned above, one gets a magnetic field B of around 0.44 T. This is in the feasible range. As already explained, however, a lower magnetic field B of, say, only around 0.05 T or more may be enough to open the hollow structures 1 nonthermally, as proposed, thanks to the thermal fluctuations.

Preferably, the magnetic field B runs at least basically perpendicular to individual surface regions of the hollow structures 1. This is always the case for the preferred hollow sphere shape, as depicted. For other shapes, especially a tubular configuration of the hollow structures, the magnetic field B should however run preferably at least basically perpendicular to the axis of the tube or rotate in such a way that the magnetic field B runs at least temporarily basically perpendicular to the axis of the tube. The same holds for other shapes of the hollow structures 1.

The preceding remarks hold accordingly for so-called ferro-fluids, especially when these form hollow structures 1. The term "magnetic nanoparticle" should therefore preferably have a broad interpretation.

The proposed nonthermal opening of the hollow structures 1 can be used quite universally and especially for the following mentioned purposes.

In the depicted example, the hollow structure 1 has a substance 5, especially a diagnostic and/or therapeutic agent, enclosed by its shell—i.e., embedded or taken up by it. Such hollow structures 1 can than be fixed or concentrated in a desired region in a fluid flow, especially in the blood circulation, by means of a magnetic field or the already-mentioned magnetic field B—depending on the gradient, the strength of the magnetic field, the flow relations, and the like—and opened by the mentioned magnetic field B as proposed in order to release the substance 5 as needed. As already explained, this produces a nonthermal opening by the strong, preferably rotating magnetic field B, which prevents an unwanted heating of the substance 5 and/or the blood or surrounding bodily tissue or the like.

The mentioned hollow structures 1 can also be used as miniaturized actuators, in which case only a onetime activation is possible. The activation or manipulation occurs by opening the hollow structures 1 by means of the strong, preferably rotating magnetic field B, as proposed.

The mentioned hollow structures 1 can also be integrated or incorporated in a material (not shown), especially a composite or the like. By opening the hollow structures 1 with the strong, preferably rotating magnetic field B, a modification of material properties can then be brought about.

The invention claimed is:

1. A method for opening of hollow structures made of magnetic nanoparticles comprising:
   exposing the hollow structures to a strong rotating magnetic field, the magnetic field not producing any significant heating of the hollow structures or the surroundings, so that the interaction of magnetic dipoles of neighboring nanoparticles comes close to or exceeds the binding energy of the neighboring nanoparticles and thereby one or more of separates the nanoparticles and opens up the hollow structures, wherein the hollow structures are unable to follow a rotation of the strong rotating magnetic field.

2. The method of claim 1, wherein the hollow structures are basically hollow spheres or hollow cylinders in shape.

3. The method of claim 1 wherein the magnetic field is greater than 0.1 T.

4. The method of claim 1, wherein the magnetic field is at least $(3\mu_0\mu)/(2\pi a^3)$, where:
   $\mu$ corresponds to the magnetic moment of the interacting nanoparticles, and a corresponds to the center-to-center distance between nanoparticles.

5. The method of claim 1, wherein the hollow structures are opened nonthermally, especially at least essentially at room or body temperature.

6. The method of claim 1, wherein the strong rotating magnetic field cuts open the hollow structures preferably along a circumference.

7. The method of claim 6, wherein a frequency of rotation of the strong rotating magnetic field is greater than 100 Hz, especially greater than 1 kHz.

8. The method of claim 6, wherein a frequency of rotation of the strong rotating magnetic field is less than 100 kHz, especially less than 10 kHz.

9. The method of claim 1, wherein the nanoparticles, especially their cores, are ferromagnetic or superparamagnetic.

10. The method of claim 1, wherein the diameter of the hollow structures is 0.1 to 10 μm, especially 1 to 5 μm.

11. The method of claim 1, wherein the hollow structures are used for the transport of a substance, such as a chemical or a drug, in a liquid flow, wherein the magnetic field is used to break open the hollow structures in a desired region, especially one that is not accessible, and thereby release the substance.

12. Magnetic nanoparticles for the making of a diagnostic and/or therapeutic agent, especially for diagnosis and/or treatment of disease, wherein a diagnostic and/or therapeutic substance is contained in hollow structures made of the magnetic nanoparticles and the hollow structures are nonthermally opened by a magnetic field in the human or animal body to release the diagnostic and/or therapeutic substance, wherein the magnetic field rotates and the hollow structures are unable to follow the rotation of the magnetic field.

13. The magnetic nanoparticles of claim 12, wherein the hollow structures are opened by exposing the hollow structures to a strong magnetic field, at least one not producing any significant heating of the hollow structures or the surroundings, so that the interaction of magnetic dipoles of neighboring nanoparticles, possibly supported by thermal fluctuations, especially those caused by the ambient heat, comes close to or exceeds the binding energy of neighboring nanoparticles and thereby separates the nanoparticles or opens up the hollow structures.

14. The method of claim 1, wherein the hollow structures are used for manipulation, and wherein the hollow structures are used as actuators which can be activated one time by the magnetic field.

15. The method of claim 1, wherein the hollow structures are used for manipulation of material properties, wherein the hollow structures are integrated in a material in order to modify its properties by applying the magnetic field and opening up the hollow structures.

16. A substance delivery mechanism comprising:
a hollow structure, the hollow structure including a plurality of magnetic nanoparticles, each magnetic nanoparticle having a magnetic core encapsulated by a non-magnetic envelope, the hollow structure housing the substance, wherein:
the substance is released by applying a rotating magnetic field to the hollow structure, the magnetic field not producing any significant heating of the hollow structure or the surroundings; and
the structure is unable to follow a rotation of the magnetic field.

* * * * *